US008859224B2

(12) United States Patent
Taninaka et al.

(10) Patent No.: US 8,859,224 B2
(45) Date of Patent: Oct. 14, 2014

(54) MICROINJECTION DEVICE AND MICROINJECTION METHOD

(75) Inventors: Kiyoshi Taninaka, Kawasaki (JP); Jun Sasaki, Kawasaki (JP); Akihiko Yabuki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1593 days.

(21) Appl. No.: 11/785,410

(22) Filed: Apr. 17, 2007

(65) Prior Publication Data

US 2008/0206802 A1    Aug. 28, 2008

(30) Foreign Application Priority Data

Apr. 26, 2006    (JP) .................................. 2006-121491

(51) Int. Cl.
*C12Q 1/02* (2006.01)
*C12M 1/42* (2006.01)
*C12M 1/34* (2006.01)

(52) U.S. Cl.
CPC ............... *C12M 35/00* (2013.01); *C12M 41/44* (2013.01); *C12M 41/00* (2013.01); *C12M 41/40* (2013.01)
USPC ......................... 435/29; 435/286.5; 435/286.6

(58) Field of Classification Search
CPC ...... C12M 35/00; C12M 41/00; C12M 41/40; C12M 41/44
USPC ...................................... 435/29, 286.5, 286.6
See application file for complete search history.

(56) References Cited

U.S. PATENT DOCUMENTS 6,479,288 B1 * 11/2002 Laffafian et al. .............. 435/455
6,499,515 B2    12/2002 Sander 2004/0182706 A1    9/2004 Li
2005/0272039 A1    12/2005 Yasuda
2007/0141593 A1 *  6/2007 Lee et al. ........................ 435/6
2011/0040279 A1 *  2/2011 Walsh ........................... 604/506

FOREIGN PATENT DOCUMENTS

| JP | 5-192171 | 8/1993 |
| JP | 2000-4869 | 1/2000 |
| JP | 2004-081084 A | 3/2004 |

OTHER PUBLICATIONS

Bobrov, G N. et al.,"Stabilised micro-dispenser for medical and biological experiments has pipette connected to pressure-to-voltage transducer at input to voltage-time transducer",Database WPI Week 197932, Derwent Publications Ltd., London, GB; AN 1979-59337B, XP002442528 Aug. 28, 1978.
http://www.eppendorf.com/int/index.php?l=21
&pb=4519f427d9efc34a&sitemap=2.1&action=product
&catalognode=33428#. (Publically Available Prior to Aug. 6, 2006).
http://www.narishige.co.jp/products/group1/im-300.htm. (Publically Available Prior to Aug. 6, 2006).

* cited by examiner

*Primary Examiner* — Susan Hanley
(74) *Attorney, Agent, or Firm* — Fujitsu Patent Center

(57) ABSTRACT

A fluorescence-intensity detecting unit detects fluorescence intensity by injecting a first solution containing a fluorescent reagent into a second solution that does not form an interface with the first solution through an injecting member. A calculating unit calculates the injection amount of the first solution from the fluorescence intensity based on a correlation between fluorescence intensities and injection amounts measured in advance. A computing unit obtains a correlation between an injection amount, pressure and pressurizing time based on the calculated injection amount. An adjusting unit adjusts the amount of the first solution to be injected into the endoplasmic reticulum by controlling pressure and pressurizing time based on the obtained correlation.

6 Claims, 8 Drawing Sheets

FIG.5
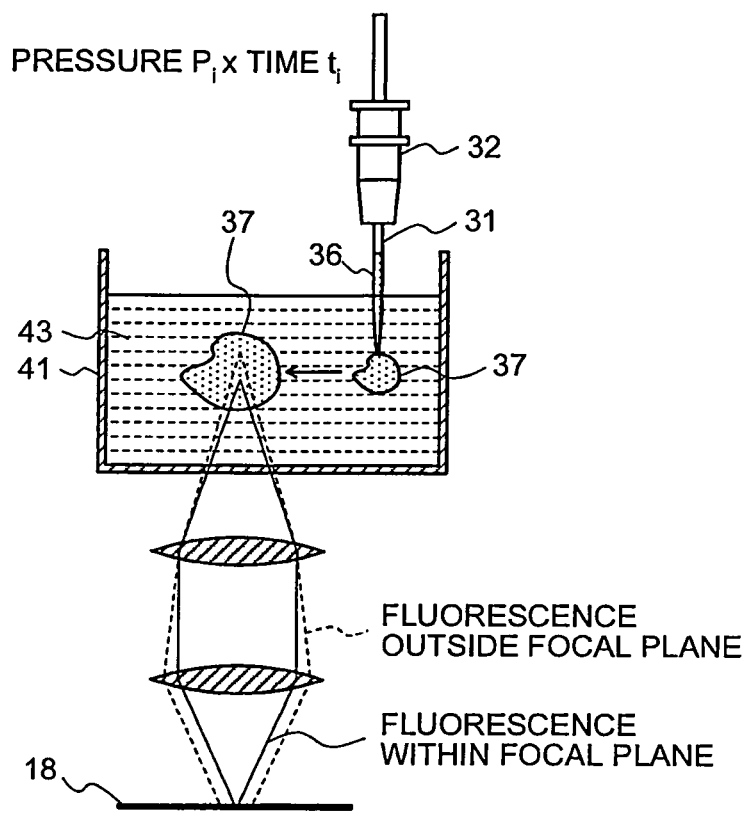
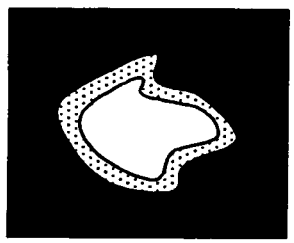
DISTRIBUTION OF FLUORESCENCE
INTENSITIES ON COOLED CCD CAMERA

MICROINJECTION DEVICE AND MICROINJECTION METHOD

CROSS REFERENCE TO RELATED APPLICATIONS

This application claims the benefit under 35 U.S.C. Section 119 of Japanese Patent Application No. 2006-121491, filed Apr. 26, 2006, which is hereby incorporated by reference in it's entirety into this application.

BACKGROUND OF THE INVENTION

1. Field of the Invention

The present invention relates to a microinjection device and a microinjection method.

2. Description of the Related Art

In the fields of biology and medicine, development of new drugs and the like requires observation of reaction to a reaction solution, cell cultivation in a culture medium, and chemical injection into a cell. Japanese Patent Application Laid-Open No.2004-081084, for example, discloses a microinjection technology to drop or inject a minute-quantity of solution such as a chemical into a culture medium or a cell with high accuracy.

Among injection devices available on the market, however, there is no product until today that is characterized in its quantifying ability in introducing a substance to a cell. This is because there is no means in principle other than microinjection for adjusting the introduction amount, and because it is difficult to adopt commonly-used measurement factors such as concentration and electric conductivity due to the volume injected to the cell as small as the order of picolitter (pl) and femtolitter (fl) and also the small flow rate.

The measurement of a substance discharged in minute quantity may be possible with a technique such as radioisotopes. Yet, it is not easy from the aspects of safety and cost to adopt it to an injecting device.

In other fields, for example, an inkjet printer realizes a discharge in units of picolitters. The inkjet printer, however, is clearly different from a microinjection device in that an inkjet printer forms an interface between ink and air.

When a substance is introduced into a cell, a solution of the substance to be introduced is injected into the intracellular fluid so that no interface is formed between the intracellular fluid and the solution of the introduced substance.

As widely known, traction exerts a significant influence upon a substance as small as, or smaller than, micrometers, and the internal pressure of a droplet increases in proportion to the curvature of the droplet.

Thus, even when the volumes of substances are the same, an inkjet printer deals with a far larger pressure by orders of magnitude. It is therefore difficult to apply the same mechanism to the microinjection.

Moreover, the inkjet printer also has a far larger maximum flow rate owing to the function of its actuator. This facilitates the measurement of the total quantity, and also the measurement of an average amount of a single injection.

As described above, the conventional microinjection technologies have a problem in quantification because, without a practical quantitative measuring technique, the adjustment of an injection amount depends on experience and guesswork by referring to the swollenness of a cell or the like.

The microinjection uses a hollow needle whose point has a diameter equal to or smaller than 1 micrometer, so small that it gradually causes clogging around the point and reduces the flow rate. There has been a problem that there is no means to quantitatively correct the flow rate.

Furthermore, the hollow needle is made of glass, and an aqueous solution therein tends to flow backward due to capillary rise. Thus, pressure opposing to the rise needs to be applied all the time. There has been a problem, however, that because the exact threshold of this pressure cannot be found out, there is no choice but to apply an excessive pressure. This causes the injection substance to run off, and there is a possibility that the run-off substance acts on a cell.

SUMMARY OF THE INVENTION

It is an object of the present invention to at least partially solve the problems in the conventional technology.

According to an aspect of the present invention, a microinjection device that includes an injecting member having a hollow point portion and introduces a substance contained in the injecting member to endoplasmic reticulum under pressure, includes a fluorescence-intensity detecting unit that detects fluorescence intensity by injecting a first solution containing a fluorescent reagent into a second solution that does not form an interface with the first solution through the injecting member, a calculating unit that calculates an amount of the first solution injected into the second solution from the fluorescence intensity based on a correlation between fluorescence intensities and injection amounts measured in advance, a computing unit that obtains a correlation between an injection amount from the injecting member, pressure and pressurizing time based on calculated injection amount, and an adjusting unit that adjusts an amount of the first solution to be injected into the endoplasmic reticulum by controlling pressure and pressurizing time based on obtained correlation between the injection amount, the pressure, and the pressurizing time.

According to another aspect of the present invention, a microinjection method applied to a microinjection device that includes an injecting member having a hollow point portion and introduces a substance contained in the injecting member to endoplasmic reticulum under pressure, includes injecting a first solution containing a fluorescent reagent into a second solution that does not form an interface with the first solution through the injecting member to detect fluorescence intensity, calculating an amount of the first solution injected into the second solution from the fluorescence intensity based on a correlation between fluorescence intensities and injection amounts measured in advance, obtaining a correlation between an injection amount from the injecting member, pressure, and pressurizing time based on calculated injection amount, and adjusting an amount of the first solution to be injected into the endoplasmic reticulum by controlling pressure and pressurizing time based on obtained correlation between the injection amount, the pressure, and the pressurizing time.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 5 is a schematic for explaining an online calibration in the microinjection method according to the first embodiment;

DETAILED DESCRIPTION OF THE PREFERRED EMBODIMENTS

Exemplary embodiments of the present invention are explained in detail below with reference to the accompanying drawings.

Figure 1:
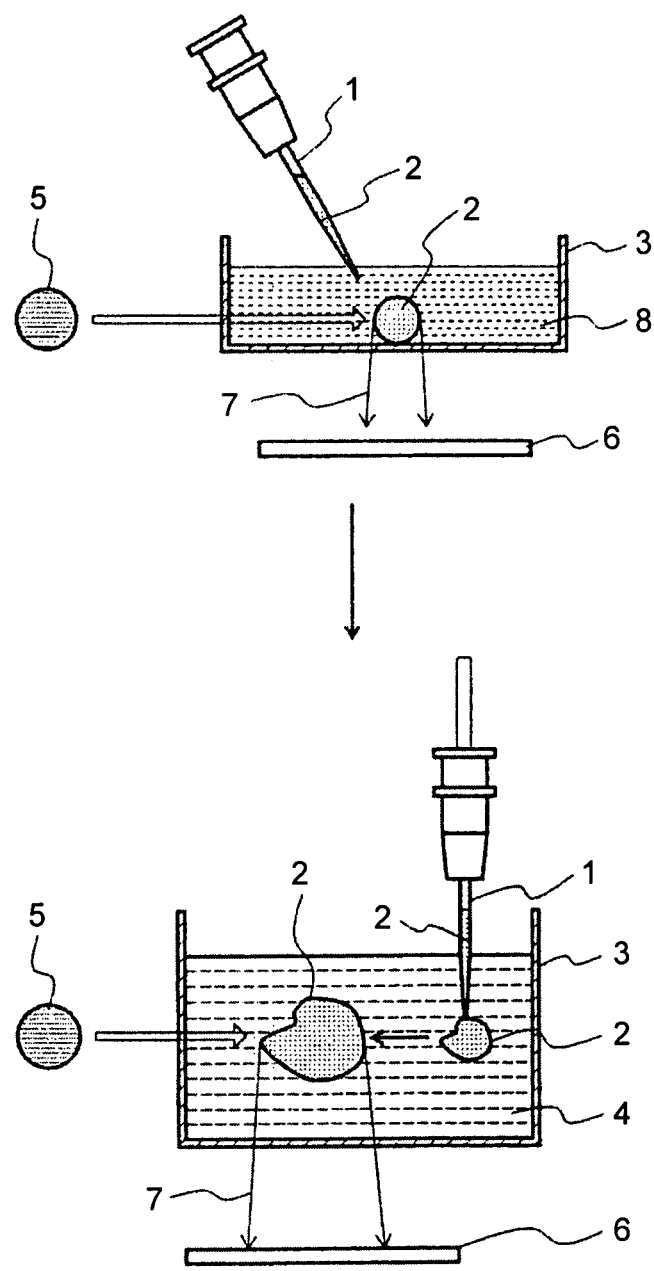
FIG. 1 is a schematic for explaining the operation of a microinjection device according to an embodiment of the present invention.

FIG. 1 is a schematic for explaining the operation of a microinjection device according to an embodiment of the present invention. The microinjection device includes an injecting member 1 having a hollow point portion, and a fluorescence-intensity detecting unit 6 that detects fluorescence intensity. In addition, it is preferable that the microinjection device include an irradiating unit 5 that irradiates a droplet with excitation light to cause the droplet to emit fluorescence 7.

Referring to FIG. 1, a first solution 2 containing a fluorescent reagent is injected through the injecting member 1 into a second solution 4 such as silicone oil in a container 3 that does not form an interface with the first solution 2 to detect fluorescence intensity. The first solution 2 is injected through the injecting member 1 into a liquid 8 that forms an interface with the first solution 2 to form a droplet. The diameter of the droplet is measured from an image obtained by photographing the droplet, and fluorescence intensity of the droplet is detected. An injection amount is calculated based on a correlation between injection amount and fluorescence intensity obtained from the diameter of the droplet and detected fluorescence intensity. The injection amount of the first solution 2 into endoplasmic reticulum is adjusted by controlling pressure and pressurizing time based on a correlation between the injection amount, pressure, and pressurizing time.

Incidentally, the term "endoplasmic reticulum" as used herein is a generic designation for cells, microorganisms, microcapsules, and the like. Examples of the injecting member 1 include a micropipette, a syringe, and a capillary. The injecting member used to inject the first solution 2 into the liquid 8 can be different from the one used to inject the first solution 2 into the second solution 4.

A microinjection method according to a first embodiment of the present invention is explained below with reference to FIGS. 2 to 6.

Figure 2:
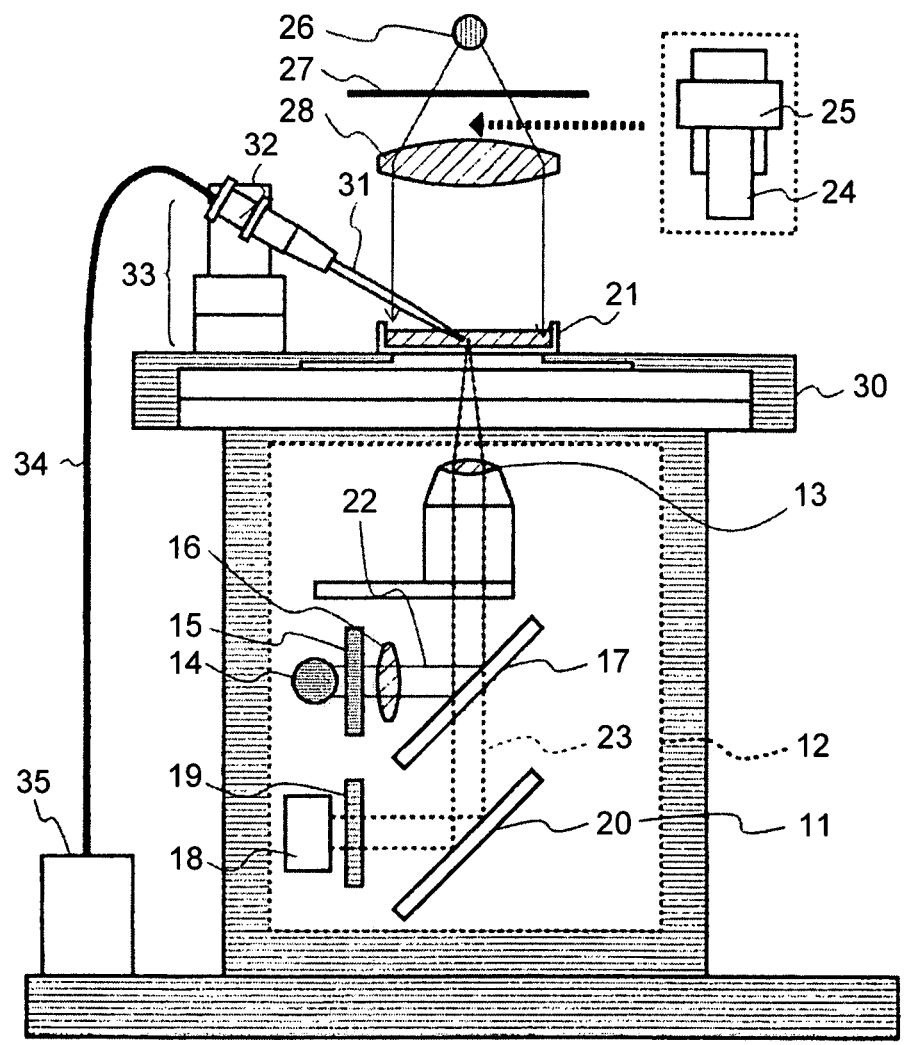
FIG. 2 is a conceptual schematic of a microinjection device according to a first embodiment of the present invention.

FIG. 2 is a conceptual schematic of a microinjection device according to the first embodiment. A base 11 includes therein a coaxial-lighting high-powered inverted microscope 12 with a focusing function that allows vertical movements of an objective lens 13. A controller-attached XY stage 30 is supported by and fixed on the base 11. The XY stage 30 transports a transparent container 21, such as a petri dish for calibration and a cell reaction chip that holds cells, to an observation position.

Inside the high-powered inverted microscope 12, an excitation light source 14, a filter 15, a collimator lens 16, and a half mirror 17 are arranged as a set, and also a cooled CCD camera 18, a fluorescence filter 19, and a reflection mirror 20 are arranged as a set.

The wavelength of excitation light 22 from the excitation light source 14 is narrowed down to, for example, 465 nanometers to 495 nanometers by the filter 15, and collimated by the collimator lens 16. Thereafter, the light is reflected by the half mirror 17 onto the side of the transparent container 21, and is brought into a converged state by the objective lens 13 to irradiate the transparent container 21.

When the solution in the transparent container 21 contains a fluorescence reagent, the excitation light 22 excites the fluorescence reagent to produce fluorescence 23. The produced fluorescence 23 is incident via the objective lens 13, the half mirror 17, and the reflection mirror 20 onto the fluorescence filter 19. The fluorescence filter 19 filters out any light wavelengths other than the wavelength of the fluorescence. Thus, the cooled CCD camera 18 kept at −70 degrees Celsius, for example, detects the intensity of the fluorescence 23 only.

A coaxial-lighting high-powered upright microscope 24 that has a focusing unit that moves an objective lens in a vertical direction along the Z axis and a CCD camera 25 that photographs a microscope image captured by the high-powered upright microscope 24 are arranged above the XY stage 30. Hence, the top surface of the transparent container 21 is observed through the bottom surface by the high-powered inverted microscope 12, and the top surface of the transparent container 21 is also observed directly by the high-powered upright microscope 24.

The coaxial-lighting high-powered upright microscope 24 includes a bright-field lighting source 26, a bright-field lighting shutter 27, and a collimator lens 28 to facilitate the observation by illuminating the top surface of the transparent container 21.

A controller-equipped transport stage 33 is arranged on the XY stage to determine the positions of a capillary tube 31 and a capillary tube holder 32. The capillary tube holder 32 is connected to a discharging mechanism 35 with a tube 34.

Figure 3:
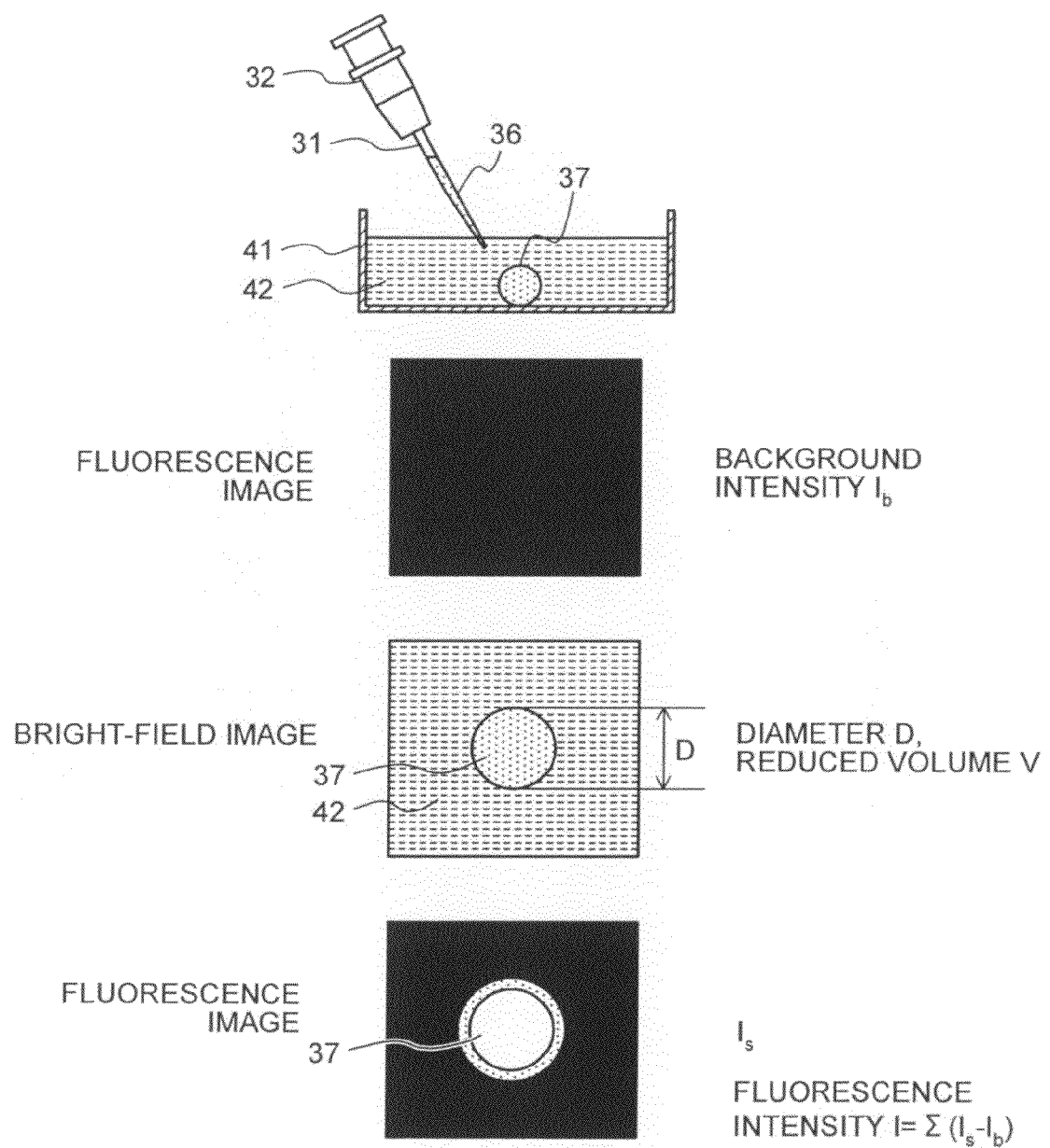
FIG. 3 is a schematic for explaining an offline calibration in a microinjection method according to the first embodiment.

FIG. 3 is a schematic for explaining an offline calibration in the microinjection method according to the first embodiment.

a. To form a droplet of a fluorescent reagent solution containing a fluorescent reagent, which will be described later, into a spherical shape, a petri dish 41 that is used as the transparent container 21 is subjected to hydrophobic treatment in advance. Otherwise, the petri dish 41 is coated to form fine nanoscopic irregularity thereon to keep the transmission from decreasing.

b. The petri dish 41 is filled with a liquid 42 such as silicone oil.

Any liquid can be adopted as the liquid 42 as long as it satisfies conditions of having a high transmittance, a low autofluorescence, and a reflective index close to that of the fluorescent reagent solution, and forming an interface with the fluorescent reagent solution.

When silicone oil is used, attention is required for the measurement time because of its hygroscopicity.

c. The capillary tube 31 is filled with a fluorescent reagent solution 36 and placed in the microinjection device.

d. At this stage, the liquid 42 in the petri dish 41 is irradiated with the excitation light 22 from the excitation light source 14, and the background image including the autofluorescence from the liquid 42 is photographed by the cooled CCD camera 18.

e. The capillary tube 31 is pressurized by the discharging mechanism 35 to drop a minute quantity of the fluorescent reagent solution 36 into the petri dish 41. A minute droplet 37 of the fluorescent reagent solution 36 is thereby formed in the bottom of the petri dish 41.

f. Using the high-powered upright microscope 24, the bright-field image is taken by the CCD camera 25. In addition, the fluorescent image including the fluorescence 23 from the droplet 37 is taken by the cooled CCD camera 18 under irradiation of the excitation light 22 from the excitation light source 14.

g. The volume V of the droplet 37 is calculated from the diameter D of the droplet 37 based on the photographed bright-field image.

The scale of the image to the actual size is obtained in advance.

h. The background intensity $I_b$ of each pixel of the background image is subtracted from the fluorescence intensity $I_s$ of each pixel of the photographed fluorescence image. The total sum I $(=S(I_s-I_b))$ is obtained by summing up the fluorescence intensities for the entire plane or an area of a certain luminance level.

i. Measurements are performed sequentially by changing the pressures to be applied by the discharging mechanism 35 to produce various diameters D for the droplet 37. A proportional curve is thereby obtained for the total sum I of the fluorescence intensities and the volume V of the droplet 37.

In the measurement, the volume V of the droplet 37 is within a range between 10 femtoliters and 100 picoliters as appropriate.

The fluorescence is emitted in all directions. However, the droplet 37 is so small that the ratio of the light entering the objective lens 13 to the entire amount of light can be considered as substantially constant regardless of the size of the droplet 37.

In addition, it is assumed that the excitation light 22 has an intensity high enough for the fluorescent elements of the droplet 37 to become saturated.

As an example of the fluorescent reagent solution 36, ALEXA FLUOR 488 (a registered trademark of Molecular Probes Inc.), fluorescent dye, is adopted. When the wavelength of the excitation light 22 is set between 465 nanometers and 495 nanometers, the fluorescence 23 with a wavelength of approximately 550 nanometers is emitted, for example.

Figure 4:
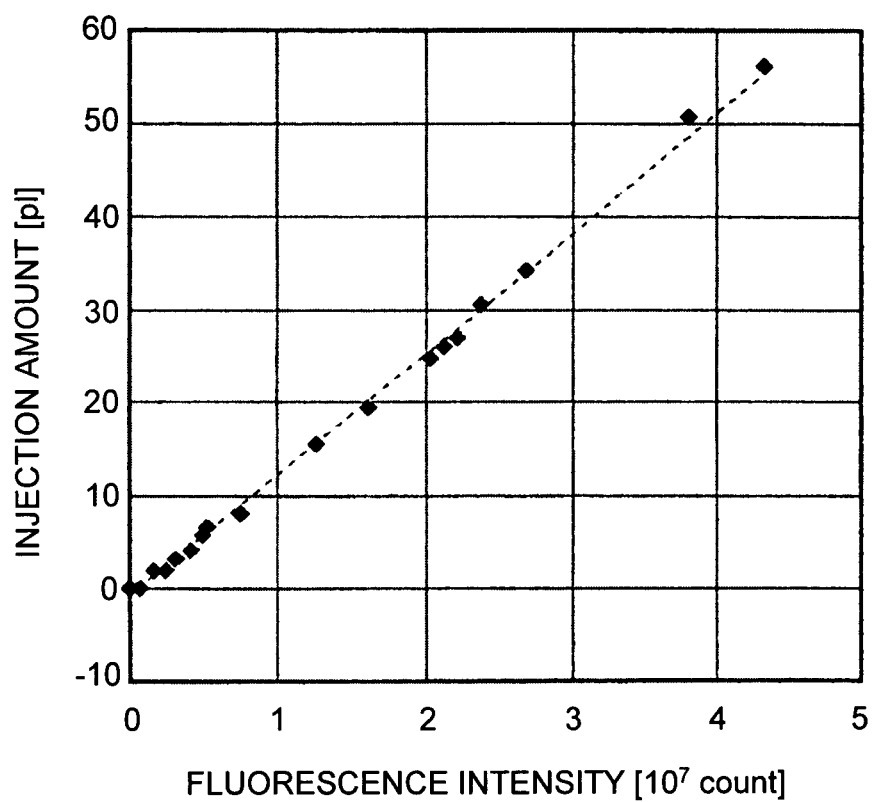
FIG. 4 is a graph of correlation between the total sum I of fluorescence intensities and the volume V of a droplet.

FIG. 4 is a graph of correlation between the total sum I of the fluorescence intensities and the volume V of the droplet indicated by a proportional line. As shown in FIG. 4, the total sum I of the fluorescence intensities and the volume V are in a proportional relation substantially satisfying:

$$V=12.5 \text{ [pl/count]} \times I \text{[count]}$$

Incidentally, because the droplet 37 is spherical, a correction is added to the gradient of the obtained line when there is a significant difference between the refractive indices of the discharged liquid and the liquid 42 in the petri dish 41.

For the sake of convenience, the unit of light intensity is indicated as [count]. This is the count value for the luminance of the cooled CCD camera 18.

If the absolute light intensity is to be found out, calibration process need to be separately performed. According to the first embodiment, however, the absolute intensity is not required because the same cooled CCD camera 18 is used.

Even when different cooled CCD cameras are used, the absolute intensity is not required if a calibration is performed based on the relative ratio of sensitivity between a cooled CCD camera and a reference cooled CCD camera.

FIG. 5 is a schematic for explaining an online calibration in the microinjection method according to the first embodiment.

First, the correlation between the injection amount and the fluorescence intensity is obtained by use of the above explained offline calibration. Then, error factors such as tolerances for the shape of the capillary tube 31 are removed, using a fluorescent reagent solution prepared by mixing a specific chemical to be introduced into a cell with a fluorescent agent, as follows:

A. The fluorescent reagent solution 36 onto which the offline calibration has been performed as described above is injected into a solution 43 in the petri dish 41, such as a solution having a composition similar to the cell fluid.

Figure 6:
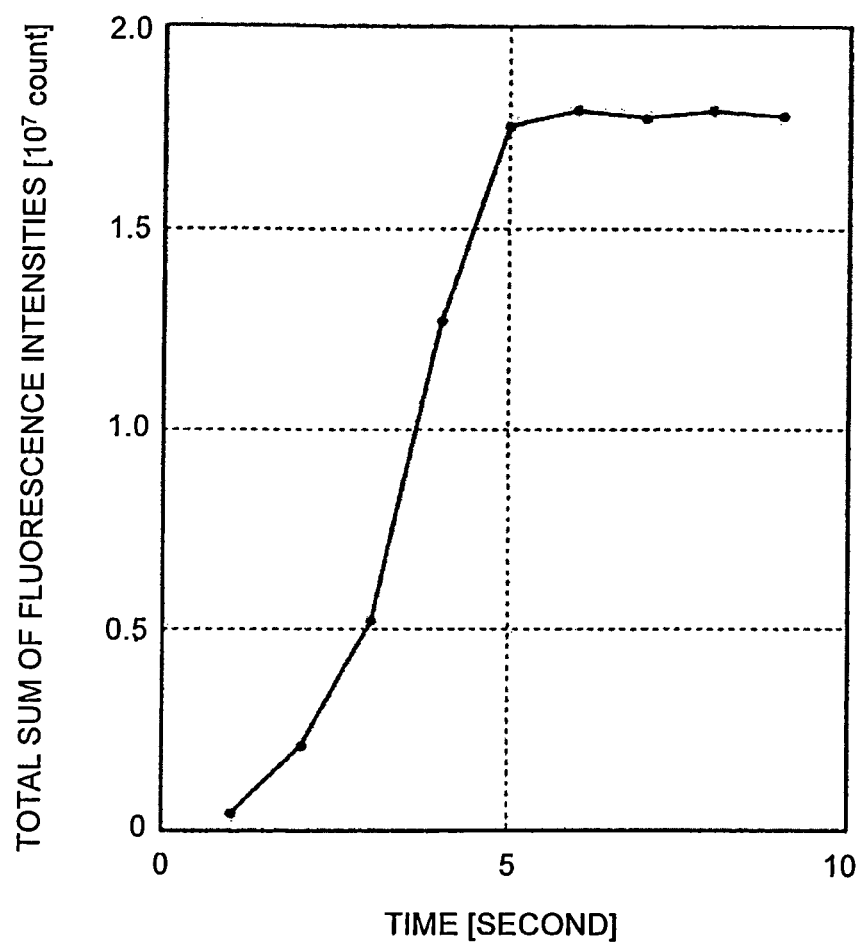
FIG. 6 is a graph of temporal variation in the total sum of the fluorescence intensities.

FIG. 6 is a graph of temporal variation in the total sum of the fluorescence intensities.

B. The injection amount is so small that sediments remain in the observation plane for several seconds. As indicated in FIG. 6, the total sum I of the fluorescence intensities is maintained to be a constant value although diffusion still continues after the injection is completed. Thus, the total sum I of the fluorescence intensities that is maintained constant is measured by the cooled CCD camera 18, and the measurement result is compared with the correlation between the total sum I of the fluorescence intensities and the volume V of the droplet depicted in FIG. 4 to convert to the injection amount.

C. Thereafter, through measurements performed in this manner by changing the pressure $P_i$ to be applied by the discharging mechanism 35 and the pressurizing time $t_i$, the injection amounts $V_i$ under different amounts of the pressure $P_i$ for different period of the pressurizing time $t_i$ are obtained.

At the steps B and C, a correlation between the pressure $P_i$, pressurizing time $t_i$ and the injection amount $V_i$ is found.

D. The conditions of the pressure and the pressurizing time that satisfy the required injection amount are interpolated or extrapolated.

After performing a calibration in the above procedure, injection is performed to the cell.

For example, although not shown in the drawings, a cell reaction chip in which several cell cultivation chambers are provided on a transparent base plate is mounted on the XY stage 30. The cell in each cell cultivation chamber together with a culture medium is brought into the field of view of the high-powered upright microscope 24. The desired amount of the fluorescent reagent solution 36 is injected into the cells through the capillary tube 31 with the pressure and the pressurizing time being controlled, while the positions of the cells are being monitored through the high-powered upright microscope 24.

As described above, according to the first embodiment, the correlation between the injection amount, the pressure, and pressurizing time is obtained by the two-step calibration, and the amount discharged through the point of the capillary tube is adjusted based on the correlation with respect to the pressure applied to the capillary tube and the pressurizing time. Thus, the injection amount can be quantitatively controlled with high accuracy.

A microinjection method according to a second embodiment of the present invention is explained below with reference to FIGS. 7 and 8.

Figure 7:
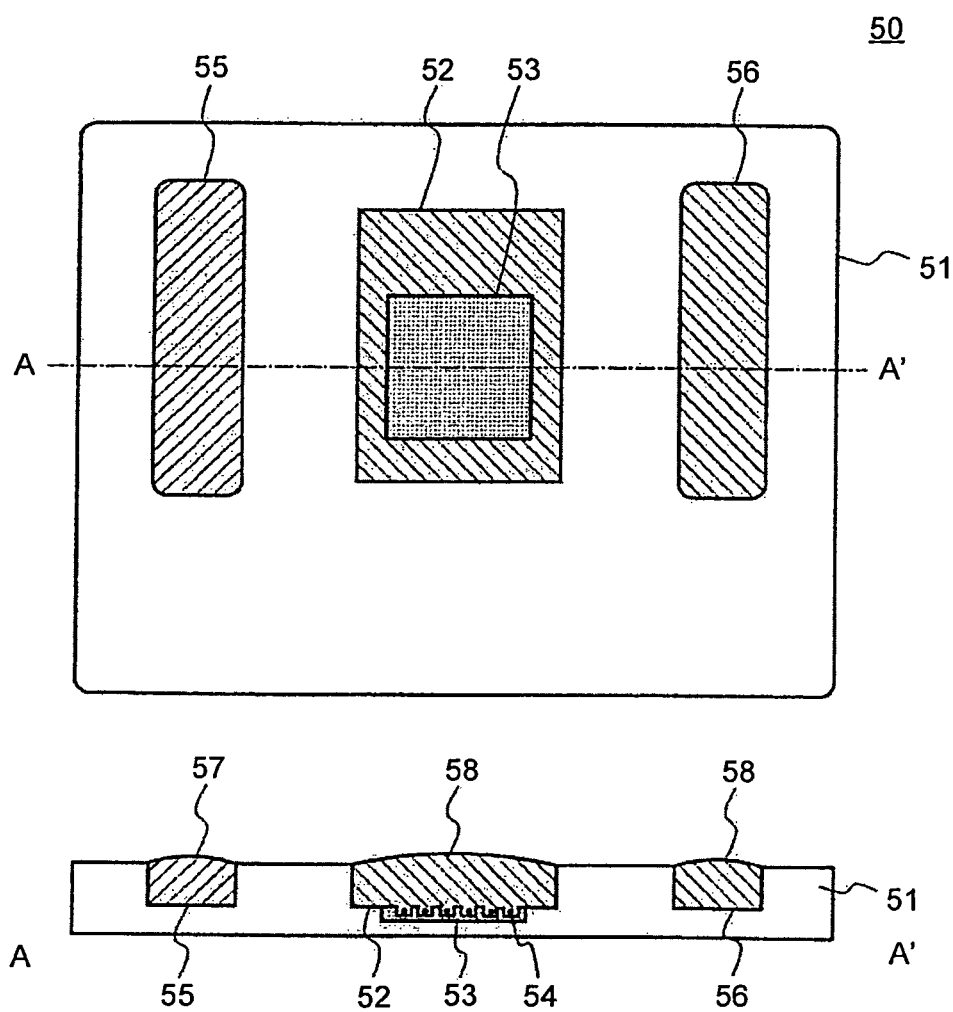
FIG. 7 is a schematic of a cell container according to a second embodiment of the present invention.
Figure 8:
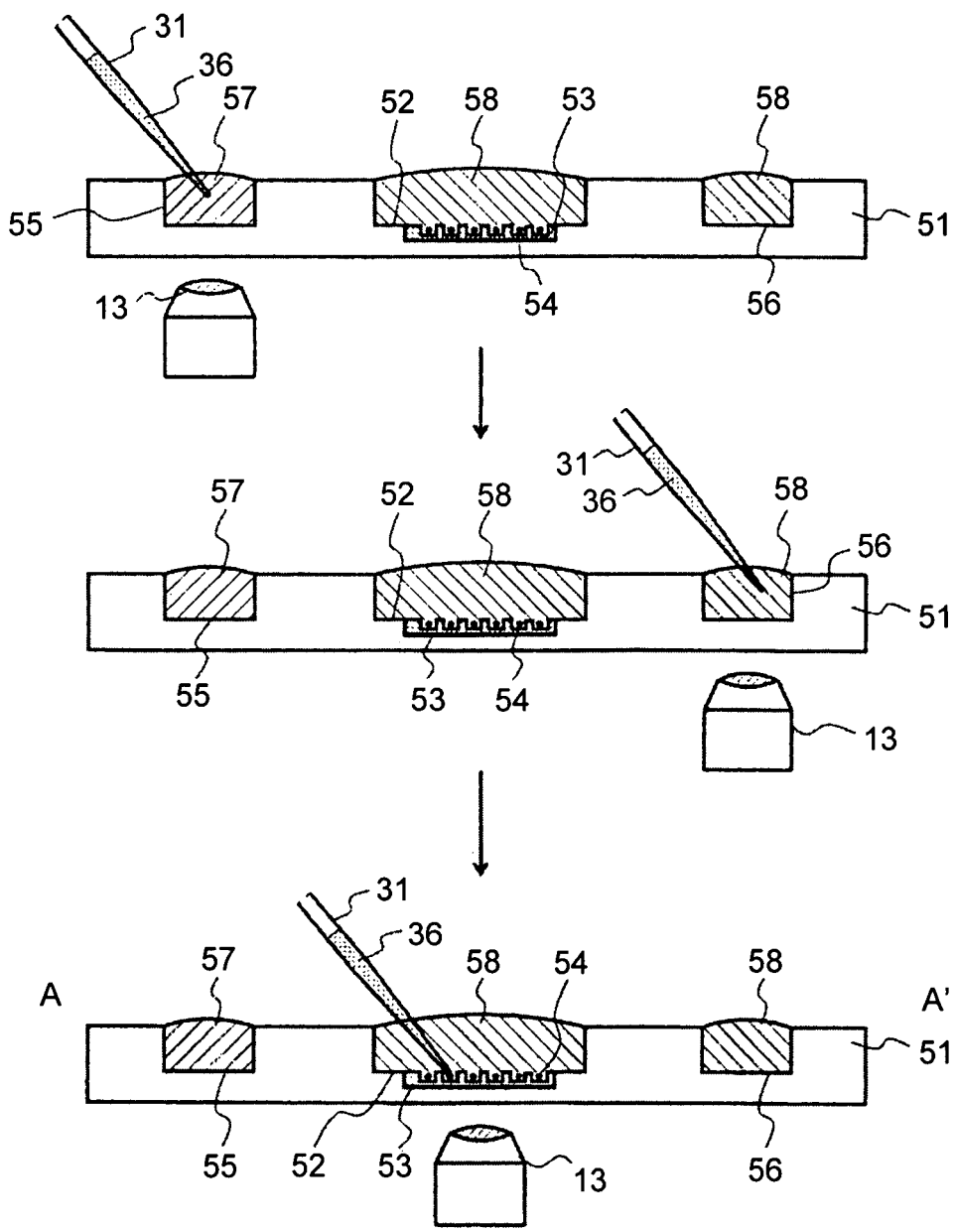
FIG. 8 is a schematic for explaining a microinjection method according to the second embodiment.

FIG. 7 is a schematic of a cell container according to the second embodiment. A cell container 50 includes a two-tiered cell-containing chamber 52, and a first measurement chamber 55 and a second measurement chamber 56, both single-tiered, which are arranged in a transparent plastic base plate 51.

The spacing between the cell-containing chamber 52 and the first measurement chamber 55, and the spacing between the cell-containing chamber 52 and the second measurement chamber 56 is determined in such a manner that the solutions in the chambers do not mix with each other.

A silicon cell chip 53 having several cell containing portions to individually hold cells is adhered to the bottom tier of the cell-containing chamber 52.

A suction hole (now shown) is provided in the bottom of each cell containing portion of the silicon cell chip 53. Cells 54 are thereby suctioned and fixed via the suction openings (not shown) arranged in the bottom tier of the cell-containing chamber 52.

When injection is performed by use of the cell container 50, the first measurement chamber 55 is filled with, for example, silicone oil 57. The fluorescent reagent solution 36 is dropped into the silicone oil 57 by use of the capillary tube 31 to calculate the correlation between the injection amount and the fluorescence intensity.

Next, the second measurement chamber 56 is filled with, for example, a culture medium 58. The fluorescent reagent solution 36 is dropped into the culture medium 58 by use of the capillary tube 31. The fluorescence intensity is measured and compared with the correlation between the total sum I of the fluorescence intensities and the volume V of droplet calculated from the first measurement chamber 55. It is thereby converted to an injection amount.

Next, through measurements performed in this manner by changing the pressures $P_i$ to be applied by the discharging mechanism and the pressurizing time $t_i$, the injection amounts $V_i$ under different amounts of pressure $P_i$ for different periods of pressurizing time $t_i$ are obtained.

Based on the above result, the fluorescent reagent solution 36 is injected into the cells 54 as adjusting the pressure $P_i$ and the pressurizing time $t_i$ to bring the injection amount $V_i$ from the capillary tube 31 to a desired level.

According to the second embodiment, because the cell container 50 includes the first measurement chamber 55 and the second measurement chamber 56, the whole two-step calibration process can be performed online. Thus, injection is always conducted with high accuracy.

This is effective especially when the fluorescent reagent solution 36 is reacted simply by being brought into contact with the cells 54 without being injected into the cells 54.

While, in the above embodiment, an online calibration is performed by use of a petri dish and only microinjection is performed thereafter, the online calibration process can be repeated as required during the microinjection process.

When the cell container of the second embodiment is used, calibration can be performed by use of the second measurement chamber every time injection to a predetermined number of cells is completed.

In this case, if the clogging situation in the capillary tube proceeds and reduces the injection amount, the amount discharged from the capillary tube is measured in real time. At least one of the pressure to be applied on the capillary tube and the pressurizing time is corrected based on the measured amount. Thus, the amount discharged from the capillary tube can be maintained substantially constant.

If the fluorescent reagent solution is not reactive only by a contact with the cells, one of every few cell containing chambers of a cell reaction chip in which cell containing chambers are arranged in a two-dimensional matrix can be used as a calibration chamber. Then, the fluorescent reagent solution is dropped into a solution such as a culture medium contained in the calibration chamber to measure the fluorescence intensity so that the amount discharged from the capillary tube can be measured in real time. At this time, whether a cell is present in the calibration chamber does not matter.

According to the first embodiment, the offline calibration is performed by use of a microinjection device for performing microinjection. However, it can be performed with a different device because the offline calibration is only to obtain the correlation between the injection amount, or the volume of the droplet, and the total sum of the fluorescence intensities.

According to the first embodiment, the measurement of the fluorescence intensity is performed online in a solution that does not form an interface with the fluorescent reagent solution. However, it can be performed offline in advance. In addition, a capillary tube with the same specifications as the capillary tube used for the microinjection but is different therefrom can be used.

In the embodiments, as a liquid that forms an interface with the fluorescent reagent solution, silicone oil is cited by way of example and without limitation. Any liquid that forms an interface with the fluorescent reagent as with the silicone oil can suffice. For example, liquid paraffin can be used.

In the embodiments, the explanation focuses on a process of injecting a chemical into a cell, but the present invention is not limited to the injection process. For example, the present invention can be applied to the case of observing reaction of the cell by dropping a fluorescent reagent solution or the like into a cell suspension.

The measurement of the injection amount, which is performed to adjust the amount of solution injected into endoplasmic reticulum, can be performed online at the time of injecting the solution to the endoplasmic reticulum. With this, microinjection can be performed with a high degree of accuracy all the time.

In this case, if the solution containing fluorescence reagent acts on the endoplasmic reticulum only by touching it without being injected therein, the container holding the endoplasmic reticulum can include an endoplasmic reticulum holding unit, and a measuring unit arranged at a position spaced from the endoplasmic reticulum holding unit to prevent the solutions from mixing each other. The correlation between the injection amount, the pressure, and the pressurizing time can be obtained by the measuring unit. Thus, regardless of the properties of the solution, online calibration is always realized.

Otherwise, the measurement of the injection amount for adjustment of the amount of the solution injected into endoplasmic reticulum can be performed offline before the solution is injected into the endoplasmic reticulum.

As set forth hereinabove, according to an embodiment of the present invention, a solution containing a fluorescent material is used as a solution to be introduced, and a minute injection amount thereof is accurately measured based on a correlation between the injection amount and fluorescence intensity to control pressure and pressurizing time. Thus, the injection amount can be readily quantified.

Moreover, a microinjection device having the above structure can detect fluctuations in fluorescence intensity online caused by clogging or the like in the middle of the process. By performing a calibration each time fluctuation is detected, the injection amount can be maintained constant.

Furthermore, the pressure that is applied to suppress capillary rises can be quantified. Thus, fluctuations in introduction amount, unnecessary runoff that may be caused by injection during waiting time, and changes in backflow can be suppressed.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A microinjection method applied to a microinjection device that includes an injecting member having a hollow point portion and introduces a substance contained in the injecting member to a solution including endoplasmic reticulum, the microinjection method comprising:

measuring a correlation, for a first solution, between fluorescence intensity and injection amount, the measuring including:
- injecting the first solution containing a fluorescent reagent into a second solution that forms an interface with the first solution through the injecting member to form a droplet of the first solution;
- irradiating the first solution with excitation light;
- measuring a diameter of the droplet from an image of the droplet;
- detecting fluorescence intensity of the droplet; and
- obtaining the measured correlation between fluorescence intensity and injection amount from the measured diameter of the droplet and the detected fluorescence intensity;

injecting the first solution into a third solution that does not form an interface with the first solution through the injecting member, and measuring pressure and pressurizing time;

irradiating the third solution including the first solution with excitation light;

detecting fluorescence intensity of the first solution included in the third solution;

calculating an injection amount of the first solution injected into the third solution from the detected fluorescence intensity and the measured correlation;

obtaining a correlation between an injection amount of the first solution from the injecting member, pressure, and pressurizing time based on the measured pressure and pressurizing time and the calculated injection amount; and adjusting an amount of the first solution injected into the third solution including the endoplasmic reticulum by controlling pressure and pressurizing time based on the obtained correlation between the injection amount, the pressure, and the pressurizing time.

2. The microinjection method according to claim 1, wherein the first solution is injected into the third solution at the injecting through an injecting member different from the injecting member used to inject the first solution into the third solution at the adjusting.

3. The microinjection method according to claim 1, wherein the measuring, the injecting, the irradiating, the detecting, the calculating, the obtaining and the adjusting are performed while injecting the first solution into the third solution.

4. The microinjection method according to claim 1, wherein
- a container that contains the endoplasmic reticulum includes a holding unit that holds the endoplasmic reticulum and a measuring unit that is arranged at a position separated from the holding unit to prevent solutions therein from mixing each other, and
- the obtaining includes obtaining the correlation between the injection amount, the pressure, and the pressurizing time by the measuring unit.

5. The microinjection method according to claim 1, wherein the measuring, the injecting, the irradiating, the detecting, the calculating, the obtaining and the adjusting are performed before injection of the first solution into the third solution.

6. The microinjection method according to claim 1, wherein the endoplasmic reticulum is selected from the group consisting of cells, microorganisms and microcapsules.

* * * * *